(12) United States Patent
Townsend

(10) Patent No.: US 8,464,500 B2
(45) Date of Patent: Jun. 18, 2013

(54) PROCESS FOR REPROCESSING SOILED ANIMAL BEDDING

(76) Inventor: Shelly Ann Townsend, Paris, KY (US)

( * ) Notice: Subject to any disclaimer, the term of this patent is extended or adjusted under 35 U.S.C. 154(b) by 672 days.

(21) Appl. No.: 12/653,288

(22) Filed: Dec. 11, 2009

(65) Prior Publication Data

US 2010/0212262 A1    Aug. 26, 2010

Related U.S. Application Data

(60) Provisional application No. 61/154,697, filed on Feb. 23, 2009.

(51) Int. Cl.
*B65B 63/02* (2006.01)
*B65B 55/00* (2006.01)
*A01K 1/015* (2006.01)

(52) U.S. Cl.
USPC ............... 53/428; 53/438; 119/172; 119/174; 134/42; 209/10

(58) Field of Classification Search
USPC ............... 53/428, 436, 437, 438, 111 R, 521, 53/525, 527; 134/10, 33, 42; 119/171, 172, 119/174; 209/10
See application file for complete search history.

(56) References Cited

U.S. PATENT DOCUMENTS

| | | | | |
|---|---|---|---|---|
| 3,853,622 A | * | 12/1974 | Rutten | 134/25.4 |
| 4,038,944 A | | 8/1977 | Trucci | 119/458 |
| 4,201,128 A | * | 5/1980 | Whitehead et al. | 100/45 |
| 4,205,624 A | * | 6/1980 | Yacus | 119/174 |
| 4,625,679 A | * | 12/1986 | Hill | 119/172 |
| 5,195,465 A | * | 3/1993 | Webb et al. | 119/172 |
| 5,232,584 A | | 8/1993 | Wang et al. | 210/139 |
| 5,352,780 A | | 10/1994 | Webb et al. | 536/56 |
| 5,429,073 A | | 7/1995 | Ballard | 119/171 |
| 5,720,393 A | | 2/1998 | Wedel et al. | 209/13 |
| 6,044,980 A | * | 4/2000 | Houle | 210/396 |
| 6,099,660 A | | 8/2000 | Davis et al. | 134/21 |
| 7,225,757 B1 | | 6/2007 | Fagan | 119/171 |
| 7,334,345 B2 | | 2/2008 | Lasonde | 34/181 |
| 7,410,454 B1 | | 8/2008 | Levine | 493/373 |
| 2001/0032595 A1 | * | 10/2001 | Lloyd | 119/171 |
| 2003/0192485 A1 | * | 10/2003 | Opfel | 119/526 |
| 2003/0192816 A1 | | 10/2003 | Opfel | 209/133 |
| 2004/0084064 A1 | * | 5/2004 | Verderosa et al. | 134/10 |
| 2004/0121114 A1 | * | 6/2004 | Piana et al. | 428/85 |
| 2005/0016062 A1 | | 1/2005 | Bonnell-Rickard et al. | 44/535 |
| 2005/0166857 A1 | * | 8/2005 | Deroo et al. | 119/171 |
| 2006/0027181 A1 | | 2/2006 | Ikegami et al. | 119/169 |

(Continued)

FOREIGN PATENT DOCUMENTS

| | | |
|---|---|---|
| EP | 1433379 | 6/2004 |
| GB | 2100569 | 1/1983 |

*Primary Examiner* — Stephen F Gerrity
(74) *Attorney, Agent, or Firm* — Ernest D. Buff; Ernest D. Buff & Assoc. LLC; Margaret A. LaCroix, Esq.

(57) ABSTRACT

A process and system reprocesses soiled animal bedding material commingled with animal manure. The material is to remove a preponderance of the manure. The remaining soiled bedding is washed in water and a cleaning agent, rinsed and, optionally, bleached to restore color and appearance. The resulting material is dewatered and dried to reduce its moisture content and kill any remaining pathogens. After being cleaned and sanitized, the material may be reused as bedding or further processed into pellets or other products, such as manufactured fire logs.

40 Claims, 1 Drawing Sheet

U.S. PATENT DOCUMENTS

| | | | |
|---|---|---|---|
| 2006/0243677 A1 | 11/2006 | Sheahan | 210/800 |
| 2007/0006526 A1 | 1/2007 | Cullen | 44/589 |
| 2008/0053877 A1 | 3/2008 | Gemmill | 209/615 |
| 2008/0083659 A1* | 4/2008 | Menke et al. | 209/158 |
| 2010/0193416 A1* | 8/2010 | Barbaro et al. | 210/102 |
| 2010/0212262 A1* | 8/2010 | Townsend | 53/438 |

* cited by examiner

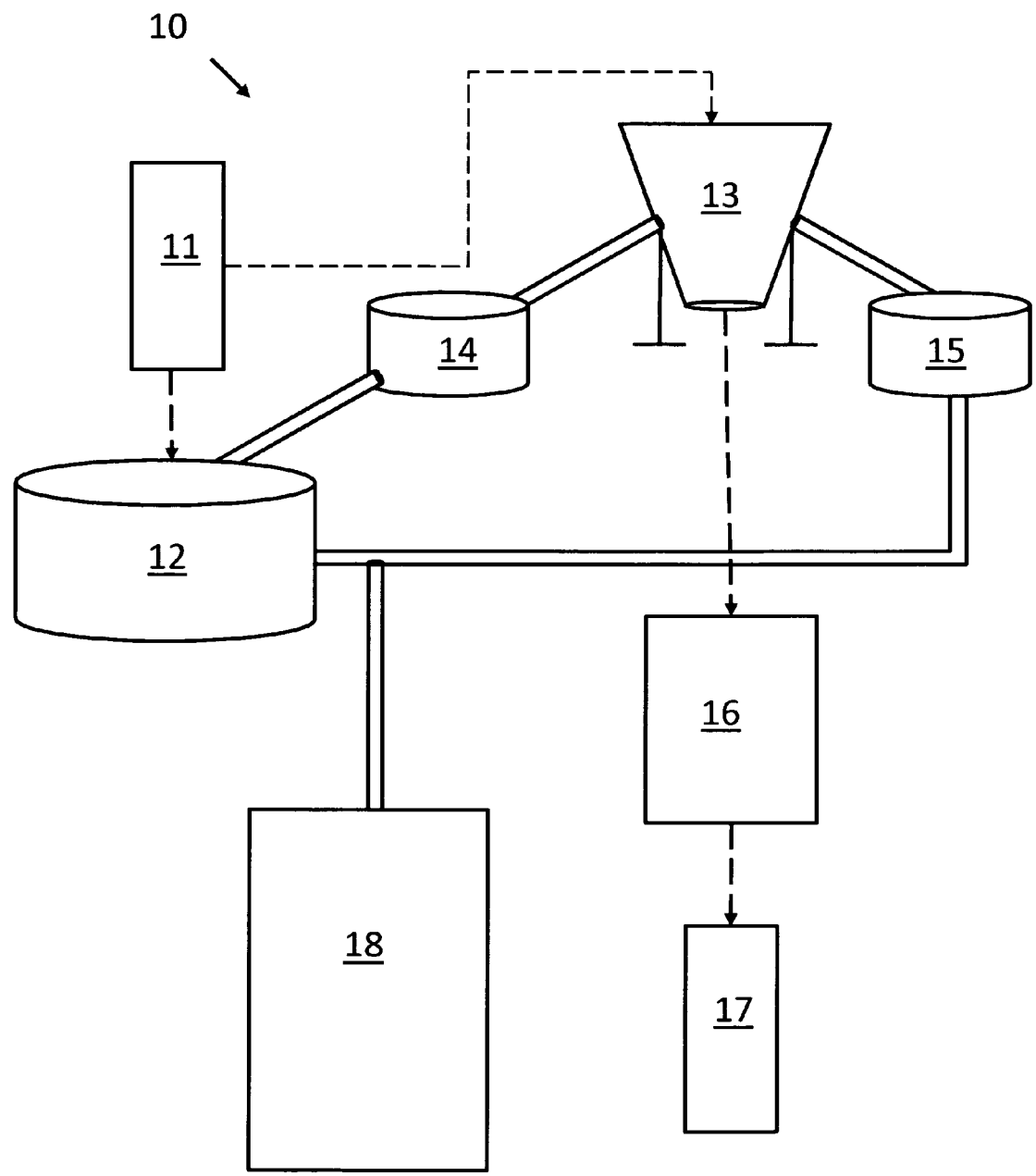

PROCESS FOR REPROCESSING SOILED ANIMAL BEDDING

RELATED U.S. APPLICATION DATA

This application claims the benefit of U.S. Provisional Application Ser. No. 61/154,697, filed Feb. 23, 2009, entitled "Recycled Animal Bedding With A Chemical Process That Returns Them Back Very Close To The Original State, And Creates A Bi-Product That Can Be Used As Fertilizer," which is incorporated herein in its entirety by reference thereto.

BACKGROUND OF THE INVENTION

1. Field of the Invention

The present invention relates to the reprocessing of animal bedding material; and more particularly to a system and process for cleaning and sanitizing animal bedding material to remove animal waste products commingled therein, permitting it to be reused as bedding or recycled as a raw material for producing other end-use products.

2. Description of Related Art

Domestic animals are widely kept by humans for pleasure, sport, or doing useful work. These animals are often housed in stalls, pens, cages, or other confining enclosures in which a bedding material is disposed on the floor to absorb the liquid and solid waste products of the animal. The absorbency of the bedding material reduces the animal's contact with the waste, improving comfort and minimizing skin irritation and disease. Large animals, such as horses, produce proportionately large amounts of waste. For example, it is estimated that a typical horse weighing about 1000 pounds may produce as much as about 30 pounds of feces and 2.5 gallons of urine daily, for a total of some 50 pounds of total raw waste per day. Soiled bedding removed with the manure during stall cleaning may account for another 8 to 15 pounds per day of waste, resulting in about 12 tons of waste a year per horse. Disposal of this matter presents serious aesthetic issues and, more importantly, environmental concerns for air and water pollution if the waste enters surface bodies of water or underground aquifers. The concerns are particularly acute for farms or other facilities that house large numbers of horses or other large animals.

Conventional practice is that animal bedding is used once and then discarded. Costs, both for producing new bedding and for disposing it after use, continue to increase. Most commonly, the materials used for animal bedding are plant-based. For livestock such as cattle and poultry, straw, hay, sawdust, kenaf, or wood shavings, or combinations thereof, are typically used. Equine bedding typically includes pressed wood pellets, wood shavings, kenaf, or sawdust. With the decline in construction and in manufacture of wood based products there has been a significant decline in the availability of wood pellets, shavings, and sawdust. As a result, bedding can be difficult to find and the cost has increased. Although certain synthetic, polymeric materials have been proposed for bedding, they have not received widespread acceptance in the agricultural community.

Along with the supply problems, costs for disposal have also increased and available techniques are constrained by environmental concerns and, in some cases, by governmental regulations.

Current methods of disposal include: i) composting, ii) spreading on land as fertilizer, iii) stockpiling near the point of generation, and iv) landfilling. Although some benefits may be derived, each of these solutions entails significant difficulties and objections. Composted manure can be used as potting soil, but the process requires a significant amount of land that is sufficiently isolated to prevent the inevitable odors from adversely impacting neighboring properties. Spreading the soiled bedding on land disperses both the waste material and the sawdust, shavings, or the like that form the base of the bedding. While the waste gradually decomposes to provide nutrients compatible with some crops, the concomitant bedding material causes dilution of the soil. As a result, dispersing the material is now being scrutinized and may ultimately be banned. Stockpiling poses a substantial risk that undesired substances may be leached into either underground aquifers or surface bodies of water. In addition, odors emanating a waste pile are objectionable. Landfill dumping incurs substantial and increasing costs for transportation and land fill operation. Moreover, many landfills do not accept manure, as it can interfere with the normal anaerobic decomposition processes if applied improperly or in excessive quantities. Governmental agencies are becoming increasingly concerned about waste management, and therefore have provided some funding through grants and low interest loans for landfill diversion.

The few processes heretofore proposed for separating animal manure and recycling used bedding are typically expensive and detrimentally alter the physical structure and appearance of the material. Thus, they have not been found satisfactory and readily accepted in the marketplace.

SUMMARY OF THE INVENTION

The present invention relates to the reprocessing of soiled animal bedding material. In various aspects, the invention provides a system and process for treating soiled bedding material to remove animal waste and provide material that can be recycled and either used again as bedding or further processed into other products.

One aspect provides a process for reprocessing soiled animal bedding commingled with manure or like animal waste products. The process comprises in sequence the steps of:
(i) separating soiled bedding and manure in a shaker device to send at least a preponderance of the manure to a holding tank and a remainder of the soiled bedding to a cleaning tank;
(ii) first washing the soiled bedding in the cleaning tank using a first washing solution comprising water and a cleaning agent, comprising first agitating the contents of the cleaning tank for a first agitating time;
(iii) draining the first washing solution;
(iv) first rinsing the soiled bedding in the cleaning tank with first rinse water for a first rinsing period;
(v) draining the first rinse water; and
(vi) drying the bedding.

The process may further comprise one or more additional cycles of washing and rinsing and/or a bleaching cycle employing a bleaching solution of water and a bleaching agent, and a rinse thereafter.

Thus cleaned, sanitized, and dried, the bedding material may be reused for bedding, and may be packaged, e.g. in bags.

It has been found that after a number of cycles of the present cleaning process, the bedding may no longer have a consistency and appearance that is desirable in the marketplace for high-end bedding applications. By using the processed material as a fuel, the need for costly and environmentally acceptable disposal is obviated and the material's energy content may be beneficially used, providing clear environmental benefits. The processed and decontaminated material is also usable as a feedstock for other applications.

Thus, in another aspect, soiled animal bedding is cleaned and further processed to form other byproducts. For example, the cleaned bedding can be further processed and compressed into compacted shapes in the form of pellets, briquettes, or other desired shapes. All these forms can be burned as fuel. Pellets additionally may be used as an alternate form of animal bedding. Similar techniques can also be used to form fire logs or fire starter logs for domestic use. As used herein, the term fire log refers to a manufactured article sized and shaped to resemble a section of a conventional log appointed for domestic use as fuel in a fireplace, wood stove, or the like. A fire starter log is a smaller, manufactured article also intended for domestic use and adapted to catch fire readily, thus facilitating the building of a fire using other fuels in a fireplace, wood stove, or the like. Fire logs and fire starter logs are herein referred to collectively as manufactured logs. Processed, sanitized bedding can be used as feedstock for other applications as well, such as particle board.

In most cases, bedding appointed for reuse must be bleached to give it the desired appearance and color. On the other hand, appearance is at most a minor issue for manufactured logs, as a dark color is ordinarily acceptable. Thus, bleaching may not be required. The washing and rinsing steps may also be omitted if the soiled bedding is destined for manufactured logs. The shaking operation removes most of the animal excrement, and what remains can be adequately decontaminated by heating and drying the bedding, e.g. in a rotary drum dryer, and with the logs compacted thereafter.

Optionally, suitable additives are included in the final manufactured log product, e.g. to give it desired appearance and mechanical integrity. The additives may also be selected to impart a pleasing aroma or to provide different colors in the flames as the product burns. Such additives may include, for example, wax and/or potpourri.

In another aspect, there is provided a system for reprocessing soiled animal bedding material commingled with animal manure to form cleaned bedding material. The system has provision for receiving water from a water source and comprises a shaker device, a holding tank, a first cleaning tank, and a dryer, wherein:
  (i) the shaker is configured to separate the soiled bedding material to send at least a preponderance of the manure to the holding tank and the soiled bedding material to the first cleaning tank;
  (ii) the first cleaning tank is configured to receive the soiled bedding material from the shaker and water from the water source and to discharge water through at least one drain;
  (iii) the first cleaning tank comprises an agitator configured to cause motion of bedding material within the first cleaning tank; and
  (iv) the dryer is in communication with the first cleaning tank to receive washed bedding material therefrom.

Optionally, the system includes a second cleaning tank so that two washing steps can be carried out in sequence by transferring material from the first cleaning tank to the second cleaning tank. The second cleaning tank is configured to receive water from the water source and to discharge water through at least one drain. It comprises an agitator configured to cause motion of bedding material within the second cleaning tank.

In some embodiments, the system includes a packaging system, such as a bagging system configured to receive the material after the cleaning and drying operations and package it into bags for storage and distribution. Alternatively, the system includes a press configured to compact the cleaned material into a compacted product, such as pellets, briquettes, or manufactured logs.

The system also optionally includes one or more waste water holding tanks that receive process water from one or more of the washing, rinsing, and bleaching cycles. The water may then be processed for reuse.

BRIEF DESCRIPTION OF THE DRAWINGS

The invention will be more fully understood and further advantages will become apparent when reference is had to the following detailed description of the preferred embodiments of the invention and the accompanying drawings, wherein like reference numeral denote similar elements throughout the several views and in which:

FIG. 1 is a schematic depiction of a process for recycling animal bedding material.

DESCRIPTION OF THE PREFERRED EMBODIMENTS

FIG. 1 illustrates one possible implementation of the present animal bedding reprocessing process, shown generally at 10. The process first involves separating soiled bedding and manure in a shaker device 11. Preferably, separation is achieved by shaking the soiled bedding to remove the fecal debris, and the shaker employs a leaf-type vibrating screener. Upon separation, the manure is removed to manure holding tank 12. The removal can be done by any suitable mechanism, including a gravity feed, a pneumatic system, or a conveyor belt arrangement. The removed manure can be composted to produce fertilizer or potting soil using known techniques.

The shaker usually employed in the first step of the present process operates by sifting the bedding to separate solid manure droppings from the soiled bedding. The incoming bedding passes through one or more screens of the shaker device with the manure sent to a holding tank 12. The manure may be allowed to fall by gravity, or a conveyor or other transport means may be used. Soiled bedding with at least a preponderance of the manure removed, then travels, e.g. using a conveyor, to cleaning tank 13.

One form of shaker useful in carrying out the separation of manure from bedding comprises a plurality of vibrating, parallel bars, rods, or tines inclined at a slight angle to the horizontal. Bedding to be separated is placed atop the bars, which are spaced apart by a distance that permits shavings or the like, but not pieces of the animal excrement, to fall between them into a collection system. The inclination and vibrating action of the bars urges the manure to migrate downward into a holding bin, yielding an efficient separation with minimal loss of soiled bedding. One useful configuration of such a separator is disclosed in U.S. Pat. No. 5,927,513 to Hart.

The present shaker is readily assembled using components such as sifters, vibrating screeners, shakers, linear screeners, separators and processing equipment available from vendors such as Smico and Triflo, that currently serve the bulk material handling industries.

Soiled bedding is transferred from the shaker system into cleaning tank 13, wherein it is treated with cleaning products and rinsed with water, preferable while undergoing slow agitation. For example, the agitation may be provided by an overhead rotary impeller. When used to process bedding material that is appointed for reuse, a relatively gentle agitation should be used to prevent overmanipulation and breakage of the bedding material. Preferably, the washing is carried out with a ratio of a volume of water used to a volume of soiled bedding being at least 1:1. More preferably the ratio is at least 2:1, and even more preferably, at least 3:1. It is preferred that the water further include a detergent, soap, or other cleaning agent, such as at least one tablespoon of a domestic laundry detergent per gallon of water, and more preferably at least two tablespoons per gallon. The present system preferably includes a cleaning agent dispenser adapted to dispense a preselected amount of a cleaning agent into the first cleaning tank. Rinsing is preferably carried out with a ratio of a volume of water used to a volume of soiled bedding of at least 1:1 and, more preferably, at least 2:1. Tank 13, as well as all other tanks in the system, preferably includes one or more drains from which liquid can be removed as needed, either by gravity or by active means such as pumps. Preferably, tank 13 is cylindrical or frustoconical in shape to permit it to act in the manner of a large washing machine vat. Tank 13 can be oriented with its cylindrical axis either vertical or horizontal. In some implementations, tank 13 can be spun rapidly to facilitate centrifugal extraction of liquid at the end of each liquid cycle. In other implementations, a compression device is present and used to squeeze the contents for tank 13 to remove liquids. As another alternative, the bedding being cleaned is transferred after draining from the cleaning tank to a separate dewatering apparatus, which extracts more liquid by centrifugal or compressive action. Suitable systems for carrying out the dewatering include those sold by The Schlueter Company, Janesville, Wis.

Preferably, all the used liquids from the cleaning, rinsing, and bleaching cycles of the present process are collected in one or more wastewater holding tanks. Although the water may be discharged, possibly after remediation needed to comply with environmental requirements, preferably it is recycled to be used in one or more steps of the present process.

Tank 13 further includes an optional hatch at its bottom that can be opened at the end of the cleaning and rinse cycles to allow the material to be removed for drying. For example, material may be directed onto conveyors carrying the material to the drying apparatus 16.

Preferably, a rotary drum drying machine is used to dry the bedding material after it is cleaned and decontaminated, but any suitable dryer capable of reaching the temperature needed to remove moisture and assure that any remaining pathogens are destroyed may also be used, for example, a grain bin with augers. At least part of the fuel for the drum or other type dryer can be provided from the bedding itself, including fines collected during the processing of the bedding. As another alternative, a continuous belt-type dryer carrying the material through a heated zone may be used. The heat source may be of any type, including heat from combustion of a fuel, resistive heating, or infrared lamps. Microwave heating may also be used. Suitable rotary drum dryers include those sold by Energy Unlimited Inc. for manufacturing wood shavings. Fuel feeder units and burners/solid fuel combustion systems/bio mass burners may be used, such as those sold by Jackson Lumber Harvester, Mondovi, Wis., under the trade name Webb Burner™, or by Energy Unlimited, Inc, Dodgeville, Wis.

The drying is typically carried out by placing the cleaned bedding material in a dryer held at temperatures of at least about 300-350° F., and preferably at about 600-800° F. The material is held at temperature in the dryer for a time sufficient to attain a required moisture level and to kill any remaining pathogens. At 600-800° F., the drying can often be accomplished in a matter of two to four minutes. After the reprocessed bedding is dried to a desired moisture level, the reprocessed, clean bedding is bagged or otherwise packaged at 17. Typically, wood shavings are dried to a moisture level ranging from about 12 to 17% for reuse as bedding to inhibit formation of mold or mildew. The bagging step at 17 is optionally omitted if the reprocessed bedding is to be sold in bulk form.

As previously noted, the present system and method are primarily intended for reprocessing bedding material so it can be reused for the same purpose. However, other end uses are also possible. For example, after a number of reprocessing cycles, the physical character and appearance bedding may deteriorate. However, such clean reprocessed bedding material is still useful for other applications. It may be compacted using a suitable press or like apparatus into the form of pellets, briquettes, or other articles such as manufactured logs. The pellet form can be also used as bedding, or it can be directly burned as fuel. Shavings intended to be compacted are typically dried to a moisture level ranging from about 8 to 9% to promote good coherence of the material in the compacted form. Presses suitable for producing briquettes from cleaned bedding include those manufactured by Biomass Briquette Systems, LLC, Chico, Calif.

Separation of the manure and debris from the soiled bedding prior to washing can optionally be skipped and the soiled bedding with fecal matter and debris can go directly to cleaning tank 13 for processing. However, separation of the fecal matter mitigates contamination of the process water and allows for a marketable byproduct, e.g. as fertilizer or compost.

In some instances, multiple cleaning cycles are optionally employed. They may be carried out serially in a single tank or, alternatively, in a semi-continuous process using separate cleaning tanks for different cycles, with material being transferred from one tank to the next after each step. The cleaning products and water rinse beneficially improve the cleaning of the soiled bedding, substantially eliminate smell, and restore color.

It is preferred that the soiled bedding not be packed too tightly in the cleaning tank 13, lest the cleaning of the bedding is compromised. Instead, cleaning is best achieved if the bedding material is able to move around and circulate in the cleaning tank 13 during the washing, rinsing, and optional bleaching operations. Whatever material remains in the bedding after the cleaning operation is substantially non-toxic and clean. Too much material in the dryer makes it is difficult to achieve uniform drying in a reasonable time. The temperature actually attained in the bedding during the cleaning and drying steps is preferably sufficient to ensure that any feces remaining in the bedding breaks down and any pathogens are killed, without charring, discoloring, or otherwise damaging the bedding.

The cleaning agents used in the one or more washing steps may include one or more of conventional soaps, detergents (such as those used for domestic laundering), or other suitable surfactants. Further additives may be used, such as alcohol, sodium bicarbonate, or sodium carbonate. Green soaps may be used as the cleaning products to provide even more enhanced environmental benefits to the process as waste from the process itself would be minimized and/or environmentally friendly. The washing and cleaning equipment may include tanks having capacities ranging from small quantities up to over 50,000 gallons of materials, such as those offered for sale by Pittsburgh Tank & Power Company. Preferably, the tank 13 is implemented with an agitator and centrifuge machinery to clean and dewater the solid material. The agitating equipment aids in the cleaning process. Suitable impeller systems and blades are available in various RPM motor speeds, and are offered for sale, e.g. by Triflo. The cleaning tank 13 preferably acts as a large washing machine with material being transferred into and out of the tanks by conveyor belts, pneumatic systems, loading equipment, or the like. A conveyer with sides is preferred to be used in the process to avoid spillage of the bedding material or loss of bedding material during conveying.

One particularly efficacious cleaning detergent that may be used is sold under the trade name SA8 Bio Quest laundry detergent. Other chemicals can be used, such as alcohol, hydrogen peroxide, PineSol® cleaner, OxyClean® powder, and any laundering, dishwashing detergent, soap nuts or magnetic laundering device. The washing, rinsing, and bleaching process steps may be carried out in vats or laundering machines, textile laundering machines. Drying may be accomplished using any suitable source of heat, such as a bin with a device such as an auger system to turn the contents during the heat drying.

The preferred duration of the washing cycle and whether a second washing cycle is needed, depends, in part, on the intended use of the cleaned bedding. For material appointed to be recycled as bedding, a second cycle and longer duration are preferred to provide material with substantially the same color and appearance as raw bedding. Inclusion of a bleaching cycle is also preferred to further enhance appearance. On the other hand, color and appearance are less critical for material to be formed into pellets, briquettes, or logs for fuel, so that only a single short cycle is needed to substantially remove all vestiges of the animal waste.

A bleaching operation is optionally included in the process, either as a discrete step or as part of at least one of the washing steps. For the latter, the washing or rinsing solution may include a bleaching agent in addition to water and some surfactant. Preferred bleaching agents include chlorine-containing agents, such as chlorine gas, chlorine dioxide, or sodium hypochlorite. The present system may include a system for on-site generation of chlorine gas as it is needed. Such a system is economically beneficial and eliminates the hazards involved in transporting and storing chlorine (either as a gas or liquid) or other chlorine-containing agent. Sodium hydroxide, a known byproduct of most industrial processes for producing chlorine gas, may be used as part of the present process or sold for other uses. Preferably, bleaching is carried out in a separate bleaching step by soaking the bedding in a chlorine-containing bleaching solution, and thereafter rinsing the bedding with water. Preferably, bleaching is carried out after at least one washing cycle, and most preferably after all washing steps are completed. The concentration and type of bleaching agent used are selected to achieve the desired level of restored coloration to the bedding, without causing breakdown of the structural integrity of the shavings or like bedding material. The present system preferably comprises a bleaching agent dispenser adapted to dispense a preselected amount of a bleaching agent into the first cleaning tank.

If a chlorine bleaching agent is used, both the waste water and bedding are beneficially dechlorinated using a sulfur-based dechlorinating agent. A preferred agent is sodium thiosulfate, which is relatively benign and non-toxic. Alternative agents include other thiosulfate salts or sulfite, bisulfite, and metabisulfite metal salts, preferably of the alkali or alkali earth metals. These agents may be introduced either from aqueous solution or as solids. The waste water is treated with an amount of dechlorinating agent sufficient to reduce the chlorine or chlorine-containing compounds, including halogenated alkanes, in the waste stream to environmentally acceptable levels. Preferably, enough dechlorinating agent is used to substantially neutralize the chlorine content. It is also preferred that any residual chlorine bleaching agent in the cleaned bedding material be neutralized to prevent any harm or discomfort to animals for whom the recycled bedding is provided.

It is preferred that waste water from the various washing, bleaching, and rinsing steps be collected in one or more waste water holding tanks. The waste water is preferably recycled in a closed loop system to minimize consumption. If needed, the recycled water can be remediated as part of the process. Some waste water can also be mixed with the manure to create a liquid fertilizer product. Alternatively, the water can be disposed after any remediation necessary for environmental compliance.

Used chemical tank 14 and used liquid tank provide storage for used process liquids. Suitable processing and remediation may be given these liquids, to permit them either to be recycled in the continued operation of the present system, used as input for liquefying the removed manure to form fertilizer, or discharged as acceptable effluent.

While the animal waste separated from bedding may be disposed of, burned, or otherwise discarded, it is preferred that it be recycled for secondary use by processing it into liquid fertilizer or composting. Some or all of the process water used in the present method may be blended with the manure to make liquid fertilizer. Alternatively, composting may be carried out by any suitable technique, including windrowing or with in-vessel techniques. In the present process, use of a mechanical separator to segregate the manure is beneficial for composting, as removal of the carbon-rich shavings reduces the ratio of carbon to nitrogen in the incoming material, yielding a superior output composted material that does not degrade agricultural soils. The presence of the shavings also markedly slows the composting. It is generally found that manure by itself will compost in one to two months, whereas mixed material requires three months or more to be fully composted. In-vessel techniques are also generally more efficient in promoting rapid composting than windrowing, and they beneficially reduce the emission of noxious odors. Careful control of temperature and aeration in an in-vessel composting process also reduces the emission of certain greenhouse gasses, including methane and other volatile organic compounds.

The present system can be mounted in a fixed installation. It is also possible to dispose the equipment on a trailer or like conveyance, permitting it to be moved to different sites. By moving the equipment closer to barns in which the bedding is used, the cost and difficulty of transporting used bedding is eliminated, and the now-cleaned bedding can be reused, again without incurring any need to transport it. In addition, the need for packaging can often be eliminated, as the cleaned material can be conveniently stockpiled pending use.

The following examples are provided to more completely describe the system and method described herein. The specific techniques, conditions, materials, proportions and reported data set forth to illustrate the principles and practice of the invention are exemplary only and should not be construed as limiting the scope of the invention.

Example

Soiled bedding in the form of wood shavings used in a horse stall and containing horse manure is cleaned using a series of washing, rinsing, and bleaching steps. A bag containing approximately 50 gallons of used bedding is first run through a shaking operation to separate most of the manure from the remaining bedding. A gallon of the soiled bedding from which the manure is substantially removed is then placed in a cleaning vessel having a capacity of about five gallons and there washed in about three gallons of a washing solution comprising water to which a quarter-cup of liquid domestic laundry detergent is added per gallon of bedding. The soiled bedding is agitated in the solution for 20 minutes. Then the vessel is drained and refilled with two gallons of rinse water. The soiled bedding agitated periodically during a 20 minute rinse cycle. Thereafter, three-quarters of a cup of 12.5% sodium hypochlorite bleach is added to bleach the shavings to substantially restore their original color and appearance and kill pathogens remaining. Alternatively, chlorine gas (about twenty grams per gallon soiled bedding processed) is used as the bleaching agent. After about ten minutes, the bleaching operation has restored the color of the shavings. Then, sufficient neutralizer in the form of a solution of 3 grams of sodium thiosulfate per gallon of water is added to neutralize the residual chlorine present from the bleach. After neutralization, the characteristic smell of chlorine is no longer perceptible. Conventional chlorine test strips are used to confirm complete neutralization. The now cleaned and sanitized bedding is dewatered and heated in an oven held at 350° F. for about one hour to dry it and kill any remaining pathogens. Alternatively, the drying is carried out for about 2-4 minutes in a rotary drum dryer held at 600-800° F. for 2-4 minutes.

The resulting bedding material has substantially the same texture, color, and appearance as fresh wood shaving bedding, demonstrating that it is suitable for reuse as bedding.

Having thus described the invention in rather full detail, it will be understood that such detail need not be strictly adhered to, but that additional changes and modifications may suggest themselves to one skilled in the art. It is to be understood that the present system and process may be implemented in various ways, using different equipment and carrying out the steps described herein in different orders. For example, the bleaching operation might be accomplished between two washing cycles. All these changes and modifications are to be understood as falling within the scope of the invention as defined by the subjoined claims.

What is claimed is:

1. A process for reprocessing soiled animal bedding material commingled with manure to form cleaned bedding material, comprising in sequence the steps of:
    separating said soiled bedding material in a shaker to send at least a preponderance of said manure to a holding tank and a remainder of said soiled bedding to a cleaning tank;
    first washing said soiled bedding in said cleaning tank using a first washing solution comprising water and a cleaning agent, comprising first agitating the contents of said cleaning tank for a first agitating time;
    draining said first washing solution;
    bleaching said soiled bedding material with a bleaching solution comprising water and a bleaching agent, thereafter rinsing said soiled bedding with bleach rinse water;
    first rinsing said soiled bedding in said cleaning tank with first rinse water for a first rinsing period;
    draining said first rinse water;
    collecting waste water resulting from at least one of said washing, rinsing, or draining steps;
    neutralizing said bleaching solution after said bleaching step; and
    drying said bedding to form said cleaned bedding material.

2. A process as recited by claim 1, further comprising the step of:
    dewatering said bedding preceding said drying.

3. A process as recited by claim 2, wherein said dewatering is carried out by centrifugally spinning said washed and rinsed bedding.

4. A process as recited by claim 1, further comprising the step of:
    packaging said cleaned bedding material.

5. A process as recited by claim 2, wherein said dewatering is carried out by compressing said washed and rinsed bedding.

6. A process as recited by claim 1, wherein a ratio of a volume of water used in said first washing to a volume of said soiled bedding is at least 1:1.

7. A process as recited by claim 6, wherein said ratio is at least 2:1.

8. A process as recited by claim 7, wherein said ratio is at least 3:1.

9. A process as recited by claim 1, wherein said cleaning agent comprises a surfactant-containing detergent.

10. A process as recited by claim 9, wherein at least one tablespoon of said detergent is used for each gallon of said soiled bedding in said first washing solution.

11. A process as recited by claim 10, wherein at least two tablespoons of said detergent is used for each gallon of said soiled bedding in said first washing solution.

12. A process as recited by claim 1, further comprising the steps of:
    second washing said soiled bedding in said cleaning tank using a second washing solution of water and a cleaning agent, comprising second agitating the contents of said cleaning tank for a second agitating time and, thereafter draining said second washing solution; and
    thereafter second rinsing said soiled bedding in said cleaning tank with second rinse water for a second rinsing period and thereafter draining said second rinse water; and
wherein said second washing is carried out after said first rinsing.

13. A process as recited by claim 12, wherein a ratio of a volume of water used in said second washing to a volume of said soiled bedding is at least 1:1.

14. A process as recited by claim 13, wherein a ratio of a volume of water used in said second washing to a volume of said soiled bedding is at least 2:1.

15. A process as recited by claim 12, wherein said cleaning agent of said second washing solution comprises a surfactant-containing detergent.

16. A process as recited by claim 15, wherein at least one tablespoon of said detergent is used for each gallon of said soiled bedding in said second washing solution.

17. A process as recited by claim 16, wherein at least two tablespoons of said detergent is used for each gallon of said soiled bedding in said second washing solution.

18. A process as recited by claim 1, further comprising the steps of:
    after said first rinsing, transferring said soiled bedding from said cleaning tank to a second cleaning tank;
    second washing said soiled bedding in said second cleaning tank using a second washing solution of water and a cleaning agent, comprising second agitating the contents of said second cleaning tank for a second agitating time and thereafter draining said second washing solution; and
    thereafter second rinsing said soiled bedding in said second cleaning tank with second rinse water for a second rinsing period and thereafter draining said second rinse water.

19. A process as recited by claim 1, wherein said waste water is collected in a waste water holding tank.

20. A process as recited by claim 19, further comprising the step of:
   remediating said collected waste water.

21. A process as recited by claim 1, wherein said bleaching agent comprises a chlorine-containing bleaching agent.

22. A process as recited by claim 21, wherein said chlorine-containing bleaching agent is chlorine.

23. A process as recited by claim 1, wherein said bleaching is carried out as part of a washing step.

24. A process as recited by claim 1, further comprising the step of:
   collecting waste water resulting from said bleaching step.

25. A process as recited by claim 1, further comprising the step of:
   packaging said cleaned bedding material.

26. A process as recited by claim 1, further comprising the step of compacting said cleaned bedding material to form a compacted product.

27. A process as recited by claim 26, wherein said compacted product is formed as pellets.

28. A process as recited by claim 26, wherein said compacted product is formed as briquettes.

29. A process as recited by claim 26, wherein said compacted product is a manufactured log.

30. A process as recited by claim 1, further comprising the step of:
   composting said separated manure.

31. A process as recited by claim 1, wherein said bedding material comprises wood shavings.

32. A process for reprocessing soiled animal bedding material commingled with manure to form cleaned bedding material, comprising in sequence the steps of:
   separating said soiled bedding material in a shaker to send at least a preponderance of said manure to a holding tank and a remainder of said soiled bedding to a cleaning tank;
   first washing said soiled bedding in said cleaning tank using a first washing solution comprising water and a cleaning agent, comprising first agitating the contents of said cleaning tank for a first agitating time;
   draining said first washing solution;
   first rinsing said soiled bedding in said cleaning tank with first rinse water for a first rinsing period;
   draining said first rinse water;
   drying said bedding to forth said cleaned bedding material; and
   compacting said cleaned bedding material to form a compacted product, wherein said compacted product is formed as pellets.

33. A process as recited by claim 32, further comprising the step of:
   packaging said cleaned bedding material.

34. A process as recited by claim 32, further comprising the step of:
   composting said separated manure.

35. A process for reprocessing soiled animal bedding material commingled with manure to form cleaned bedding material, comprising in sequence the steps of:
   separating said soiled bedding material in a shaker to send at least a preponderance of said manure to a holding tank and a remainder of said soiled bedding to a cleaning tank;
   first washing said soiled bedding in said cleaning tank using a first washing solution comprising water and a cleaning agent, comprising first agitating the contents of said cleaning tank for a first agitating time;
   draining said first washing solution;
   first rinsing said soiled bedding in said cleaning tank with first rinse water for a first rinsing period;
   draining said first rinse water;
   drying said bedding to form said cleaned bedding material; and
   compacting said cleaned bedding material to form a compacted product, wherein said compacted product is formed as briquettes.

36. A process as recited by claim 35, further comprising the step of:
   packaging said cleaned bedding material.

37. A process as recited by claim 35, further comprising the step of composting said separated manure.

38. A process for reprocessing soiled animal bedding material commingled with manure to form cleaned bedding material, comprising in sequence the steps of:
   separating said soiled bedding material in a shaker to send at least a preponderance of said manure to a holding tank and a remainder of said soiled bedding to a cleaning tank;
   first washing said soiled bedding in said cleaning tank using a first washing solution comprising water and a cleaning agent, comprising first agitating the contents of said cleaning tank for a first agitating time;
   draining said first washing solution;
   first rinsing said soiled bedding in said cleaning tank with first rinse water for a first rinsing period;
   draining said first rinse water;
   drying said bedding to form said cleaned bedding material; and
   compacting said cleaned bedding material to form a compacted product, wherein said compacted product is a manufactured log.

39. A process as recited by claim 38, further comprising the step of:
   packaging said cleaned bedding material.

40. A process as recited by claim 38, further comprising the step of:
   composting said separated manure.

* * * * *